United States Patent
Sternby

(10) Patent No.: US 6,861,266 B1
(45) Date of Patent: Mar. 1, 2005

(54) METHOD AND DEVICE FOR CALCULATING DIALYSIS EFFICIENCY

(75) Inventor: Jan Sternby, Lund (SE)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 09/581,352

(22) PCT Filed: Dec. 2, 1998

(86) PCT No.: PCT/SE98/02212

§ 371 (c)(1), (2), (4) Date: Jun. 9, 2000

(87) PCT Pub. No.: WO99/29355

PCT Pub. Date: Jun. 17, 1999

(30) Foreign Application Priority Data

Dec. 9, 1997 (FR) .............................. 97 15818
Jun. 2, 1998 (SE) ............................... 9801963-1

(51) Int. Cl.$^7$ ................................. G01N 1/18
(52) U.S. Cl. ................ 436/178; 436/175; 436/177; 422/101; 604/4.01; 210/645; 210/646
(58) Field of Search ................. 436/174, 175, 436/177, 178; 422/101; 702/19; 604/4.01; 210/645, 646, 96.2, 739

(56) References Cited

U.S. PATENT DOCUMENTS

| | | | |
|---|---|---|---|
| 5,024,756 A | * 6/1991 | Sternby | 210/93 |
| 5,100,554 A | 3/1992 | Polaschegg | 210/647 |
| 5,399,157 A | * 3/1995 | Goux et al. | 604/4.01 |
| 5,567,320 A | 10/1996 | Goux et al. | 210/739 |
| 5,644,240 A | 7/1997 | Brugger | 324/439 |
| 6,110,384 A | * 8/2000 | Goux et al. | 210/739 |
| 6,123,847 A | * 9/2000 | Bene | 210/646 |
| 6,126,831 A | * 10/2000 | Goldau et al. | 210/646 |
| 6,156,002 A | * 12/2000 | Polaschegg et al. | 604/4.01 |
| 6,217,539 B1 | * 4/2001 | Goldau | 604/4.01 |

FOREIGN PATENT DOCUMENTS

| | | | |
|---|---|---|---|
| EP | 547025 | * | 6/1993 |
| SE | 9702074-7 | | 6/1997 |
| WO | WO95/32010 | | 11/1995 |
| WO | WO96/04401 | | 2/1996 |

* cited by examiner

Primary Examiner—Maureen M. Wallenhorst
(74) Attorney, Agent, or Firm—Lerner, David, Littenberg, Krumholz & Mentlik, LLP

(57) ABSTRACT

Methods are disclosed for calculating the concentration of a predetermined substance in the blood of a mammal including passing the blood over one side of a semipermeable membrane in a dialyser and passing a dialysis fluid on the other side of the semipermeable membrane in the dialyser to provide a dialysate, measuring the concentration of the predetermined substance in the dialysate, introducing a disturbance in the dialyser, calculating the effective dialysance of the dialyser based on the disturbance, and calculating the concentration of the predetermined substance in the blood based upon the effective dialysance. Apparatus is also disclosed for calculating the concentration of the predetermined substance in the blood.

12 Claims, 3 Drawing Sheets

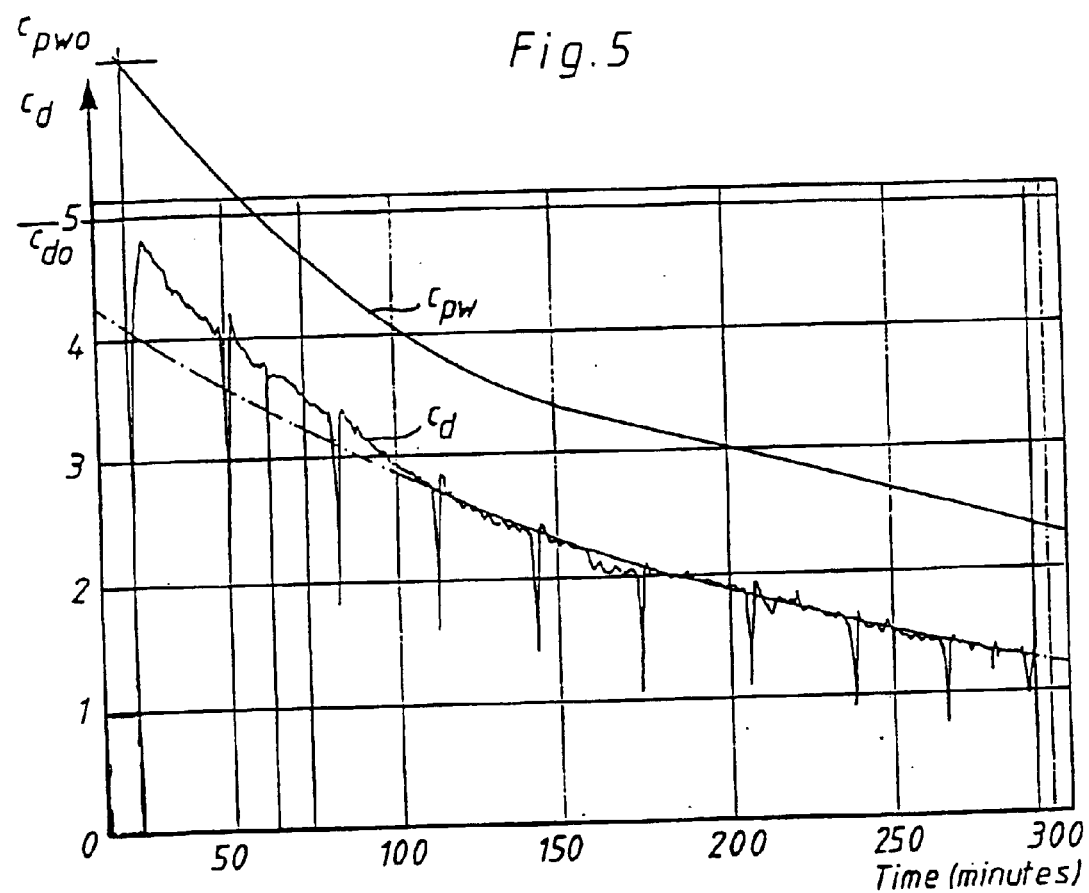

US 6,861,266 B1

METHOD AND DEVICE FOR CALCULATING DIALYSIS EFFICIENCY

FIELD OF THE INVENTION

The present invention relates to a method and apparatus for calculating dialysis efficiency. More specifically, the present invention relates to a non-invasive method and apparatus for obtaining an initial concentration of urea and/or other solutes present in blood for further calculation of dialysis parameters.

The present invention is intended to be used during dialysis treatment, such as hemodialysis, hemodiafiltration or hemofiltration. It can also be used for peritoneal dialysis treatments. However, the present invention is not limited to the above-mentioned treatment modes, but can also be used for other medical or non-medical purposes.

BACKGROUND OF THE INVENTION

A method and apparatus for calculating dialysis efficiency is disclosed in Swedish Patent Application No. 9702074-7, filed on Jun. 2, 1997, by Gambro AB. In this Swedish patent application, a whole body relative efficiency is calculated. The calculation uses a removed urea concentration curve obtained by a urea monitor during dialysis treatment. The urea monitor measures the concentration of urea in the effluent fluid from the dialyser, normally emitted to the drain. The result obtained by the urea monitor is a value of the removed mass of urea $m_{rem}$ as well as the removed urea concentration curve, from which can be calculated the total accumulated urea mass $m_0$ in the body, whole body dialysis dose Kt/V, solute removal index SRI, etc.

According to this Swedish patent application, it is necessary to obtain a value of the initial concentration of urea in blood in order to be able to fully characterise the dialysis treatment. Another approach, also described therein, is to obtain a value of the total body water volume V of the patient, whereupon the urea concentration in the blood of the patient may be calculated.

A number of different approaches to obtain the initial concentration of urea are given in this Swedish patent application, such as blood samples or equilibrated dialysis solution before the start of the treatment. These methods are more or less problematic and there is a desire to eliminate manual intervention. Moreover, blood samples need to be taken before initiation of the dialysis treatment. As soon as the treatment starts, the initial blood concentration of urea is diluted due to cardiopulmonary recirculation and access recirculation. Thus, care must be exercised to obtain the initial urea concentration before it is compromised.

The object of the present invention is to provide a method and apparatus for obtaining the initial urea concentration in blood before the dialysis treatment, to be used in the invention according to Swedish Patent Application No. 9702074-7 for calculating the essential dialysis related parameters of a patient.

SUMMARY OF THE INVENTION

Specifically, it is possible to use the total body urea mass $m_o$, obtained according to Swedish Patent Application No. 9702074-7, and the initial urea concentration $c_0$ in blood obtained according to the present invention for calculating the distribution volume V of urea in the body. This parameter V is expected to be constant from the end of one treatment to the end of the next, and could therefore be used as an alternative to dry body weight as a parameter for determining the required ultrafiltration during a dialysis treatment. Moreover, the distribution volume V may be a long term marker for the general status of the patient.

A method of determining the dialysance of a dialyser used during dialysis treatment is disclosed in According to this method, a disturbance is generated in the fresh dialysis solution before the dialyser, and the resultant effect in the dialysate after the dialyser is measured. Normally, the disturbance is induced in the conductivity of the dialysis solution. This method provides the effective ionic dialysance for the dialyser and the effective plasma conductivity.

In clinical studies this ionic dialysance for a dialyser measured according to European Application No. 658,352 has been shown to agree well with the effective plasma water clearance of that dialyser for urea ($K_e$), i.e. plasma water clearance corrected for recirculation, pulmonary recirculation as well as access recirculation.

The definition of clearance implies that the urea mass removal rate equals the product of the effective plasma water clearance ($K_e$) and plasma water concentration ($c_{pw}$) of urea in the systemic blood returning from the body. The difference between dialyser clearance and effective dialyser clearance is that for dialyser clearance the denominator should be plasma water concentration in the blood entering the dialyser while for effective dialyser clearance the denominator should be plasma water concentration in the systemic blood returning from the body. Due to recirculation this concentration in the blood entering the dialyser differs from the concentration in the systemic blood returning from the body.

The urea mass removal rate is measured by the urea monitor as the product of dialysate flow rate ($Q_d$) and the urea concentration in the spent dialysate ($c_d$). We can therefore equate the two expressions for urea mass removal rate from plasma water and into the spent dialysate $$K_e \times c_{pw} = Q_d \times c_d$$

In this equation, $K_e$ may be obtained by the method of while $Q_d$ and $c_d$ are obtained by the urea monitor. Thus, $c_{pw}$ can be calculated.

There is, however, an additional effect that has to be taken into account. Due to internal resistance in the body to urea transport, a urea gradient starts to develop within the body from the start of a dialysis treatment. This means that the urea concentrations in different parts of the body are gradually differing more and more, and the urea concentration in the blood returning from the body, which is used in the calculations above, is no longer representative of the mean urea concentration in the body. It is therefore only before or during the initiation of a treatment, while urea is equally distributed in the body, that the calculation above can be used to find the mean urea concentration in the body.

The urea monitor is programmed to find the starting value for dialysate urea $c_{d0}$ by interpolating backwards along the concentration curve using measurements from 20 to 5 minutes after the treatment start time, which is defined as the time when the measured dialysate urea concentration $c_d$ is steadily above a predetermined low concentration value. Due to time constants in the monitor this starting value will not catch the initial decrease in urea due to the development of recirculation, so this initial dialysate urea concentration $c_{d0}$ will be representative of conditions with recirculation already developed. Using this starting value of $c_d$ in the formula above, together with a measurement of effective clearance ($K_e$) performed, for example, by the method described in European Application No. 658,352, will produce the initial plasma water concentration $c_{pw0}$ of urea in the blood returning from the body. At the start, before any gradients have developed in the body, this will also be the mean plasma water concentration in the body. The measurement of effective clearance $K_e$ should preferably be performed as soon as possible after the initial 20 minutes (for the interpolation of initial dialysate urea) to avoid unintentional changes in clearance, and all factors affecting clearance such as blood and dialysate flows should be kept constant during this period.

In accordance with the present invention, these and other objects are now accomplished by the invention of a method of calculating the concentration of a predetermined substance in the blood of a mammal comprising passing the blood through one side of a semipermeable membrane in a dialyser and passing a dialysis fluid on the other side of the semipermeable membrane in the dialyser to provide a dialysate, measuring the concentration of the predetermined substance in the dialysate, introducing a disturbance in the dialyser, calculating the effective dialysance of the dialyser based on the disturbance, and calculating the concentration of the predetermined substance in the blood based upon the effective dialysance. In a preferred embodiment, the method includes determining the flow rate of the dialysate, and the calculating of the concentration of the predetermined substance in the blood comprises multiplying the measured concentration of the predetermined substance in the dialysate by the flow rate of the dialysate to provide a product and dividing the product by the effective dialysance. In accordance with a preferred embodiment, the measuring of the concentration of the predetermined substance in the dialysate is utilized to obtain a curve of the concentration over time, and the method includes calculating the initial mass of the predetermined substance in the blood, calculating the initial concentration of the predetermined substance in the blood, and calculating the distribution volume of the predetermined substance in the body by dividing the initial mass by the initial concentration of the predetermined substance in the blood.

In accordance with one embodiment of the method of the present invention, the introducing of the disturbance in the dialyser comprises changing the concentration of a second predetermined substance in the dialysis fluid, and the method includes measuring the change in the concentration of the second predetermined substance in the dialysate.

In accordance with another embodiment of the method of the present invention, the method includes determining the flow rate of the dialysate, and the introducing of the disturbance in the dialyser comprises adding a predetermined amount of a second predetermined substance into the dialysis fluid, measuring the concentration of the predetermined substance in the dialysate, determining the amount of the second predetermined substance in the dialysate by multiplying the concentration of the second predetermined substance in the dialysate with the flow rate of the dialysate to obtain a product and integrating the product over time, and the calculating of the effective dialysance comprises multiplying the flow rate of the dialysate with a fraction comprising 1 minus the amount of the second predetermined substance in the dialysate over the amount of the second predetermined substance in the dialysis fluid.

In accordance with another embodiment of the method of the present invention, the second predetermined substance comprises sodium ions, a conductivity altering substance, or urea. In a preferred embodiment, the second predetermined substance comprises urea.

In accordance with the present invention, apparatus has also been provided for calculating the concentration of a predetermined substance in the blood of a mammal comprising a dialyser including a semipermeable membrane, means for passing the blood over one side of the semipermeable membrane in the dialyser, means for passing a dialysis fluid over the other side of the semipermeable membrane in the dialyser to produce a dialysate, concentration measuring means for measuring the concentration of the predetermined substance in the dialysate, disturbance means for introducing a disturbance in the dialyser, calculating means for calculating the effective dialysance of the dialyser based on the disturbance, and concentration calculating means for calculating the concentration of the predetermined substance in the blood based on the effective dialysance. In a preferred embodiment, the apparatus includes flow rate means for obtaining the flow rate of the dialysate, the concentration calculating means comprising means for multiplying the concentration of the predetermined substance in the dialysate by the flow rate of the dialysate to provide a product, and dividing the product by the effective dialysance of the dialyser. Preferably, the concentration measuring means comprises means for measuring the concentration of the predetermined substance in the dialysate to obtain a concentration curve, and the apparatus includes mass calculating means for calculating the initial mass of the predetermined substance in the mammal, initial concentration calculating means for measuring the initial concentration of the predetermined substance in the mammal, and distribution volume calculating means for measuring the initial distribution volume of the predetermined substance in the mammal.

In accordance with one embodiment of the apparatus of the present invention, the disturbance means comprises means for changing the concentration of at least a predetermined substance in the dialysis fluid, and the apparatus includes measuring means for measuring the change in the concentration of the second predetermined substance in the dialysate.

In accordance with another embodiment of the apparatus of the present invention, the apparatus includes flow rate means for measuring the flow rate of the dialysate, and the disturbance means comprises means for introducing a predetermined amount of a second predetermined substance into the dialysis fluid, the concentration measuring means comprises means for measuring the concentration of the second predetermined substance in the dialysate, and the apparatus includes an amount determining means for determining the amount of the second predetermined substance in the dialysate by multiplying the concentration of the second predetermined substance in the dialysate with the flow rate of the dialysate to provide a product and integrating the product over time, and the calculating means comprises means for multiplying the flow rate of the dialysate by a fraction comprising 1 minus the amount of the second predetermined substance in the dialysate over the concentration of the second predetermined substance in the dialysis fluid.

In accordance with a preferred embodiment of the apparatus of the present invention, the second predetermined substance comprises sodium ions, a conductivity altering substance, and/or urea. Preferably, the second predetermined substance comprises urea.

BRIEF DESCRIPTION OF THE DRAWINGS

The present invention may be more fully understood with reference to the following detailed description, which, in turn, refers to the drawings in which:

FIG. 5 is a graphical representation of concentration values obtained from the urea monitor in the dialysis machine according to anyone of FIGS. 1–4.

DETAILED DESCRIPTION

Figure 1:
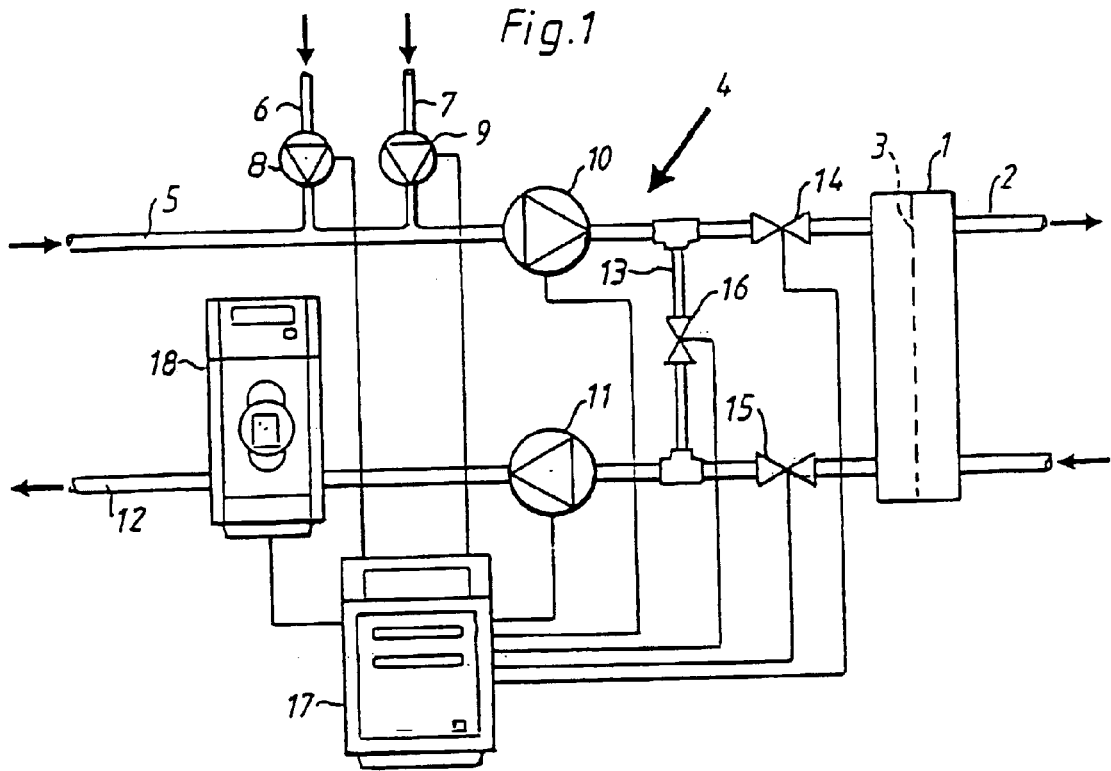
FIG. 1 is a schematic view of a dialysis machine intended for hemodialysis including a urea monitor, and in connection with which the invention can be used.

Referring to the figures, in which like reference numerals refer to like elements thereof, FIG. 1 is a schematic diagram of a dialysis machine in which the invention according to Swedish Patent Application No. 9702074-7 and the present invention can be practised. The dialysis machine provides means for replacing the renal function of a mammal if the renal function is impaired or completely absent, such as end stage renal disease of a human being.

The blood from a patient is taken out into an extracorporeal circuit 2 including a filter or dialyser 1, including a semipermeable membrane 3. The blood passes along one side of the membrane. At the other side of the membrane, a dialysis fluid is circulated by the dialysis machine 4.

The dialysis fluid is usually prepared by the machine from one or several concentrates and water to form a dialysis fluid having the desired properties. Thus, the machine disclosed in FIG. 1 comprises a water inlet 5, two concentrate inlets 6 and 7, and two concentrate metering pumps 8 and 9. A first main pump 10 propels the fresh dialysis fluid to the dialysis side of the dialyser into contact with the membrane.

A second main pump 11 passes the effluent fluid, dialysate, from the dialyser, namely the inlet dialysis fluid and any ultrafiltrate removed from the blood via the filter, further on to an outlet 12 and to the drain.

A by-pass line 13 is arranged between the first pump 10 and the second pump 11. Several valves, 14, 15 and 16, are arranged for controlling the flow of dialysis fluid. The valves and the pumps are controlled by a computer 17 as schematically shown by several lines in FIG. 1. Of course, the dialysis machine is provided with several other means as is conventional. These other means are not disclosed, since they are conventional.

The first main pump 10 is driven at a speed such that the dialysis fluid delivered to the dialyser is substantially constant, e.g. about 500 ml/min. The second main pump 11 is driven with a slightly higher speed so that the effluent fluid, called the dialysate, has a flow rate of e.g. about 515 ml/min. This operation generates a low pressure at the dialysate side of the dialyser, which is suitable for removing about 15 ml/min of ultrafiltrate fluid from the blood, i.e. plasma water. During a treatment of 4 hours, such ultrafiltration thus results in a fluid removal from the patient of 3.6 liters. Of course, the dialysis machine is operated so that the treatment prescribed to the patient is fulfilled.

In the effluent line from the dialysis machine is placed a urea monitor 18, which measures the urea concentration $c_d$ in the effluent dialysate. The monitor can be positioned inside the dialysis machine or completely outside the dialysis machine. The urea monitor may be of the type disclosed in International Application No. WO 96/04401.

The urea monitor is shown connected to the computer 17 of the dialysis machine. However, the monitor may have a computer of its own.

The urea monitor or the dialysis machine also includes means for measuring the flow rate of the effluent dialysate, $Q_d$. The computer 17 is arranged to provide concentration values $c_d$ as well as values of the total mass of urea U removed during the treatment as the integral of $Q_d \cdot c_d$. The concentration values are taken continuously so that a concentration curve $c_d$ is obtained from the urea monitor as well as a mass curve U.

Figure 2:
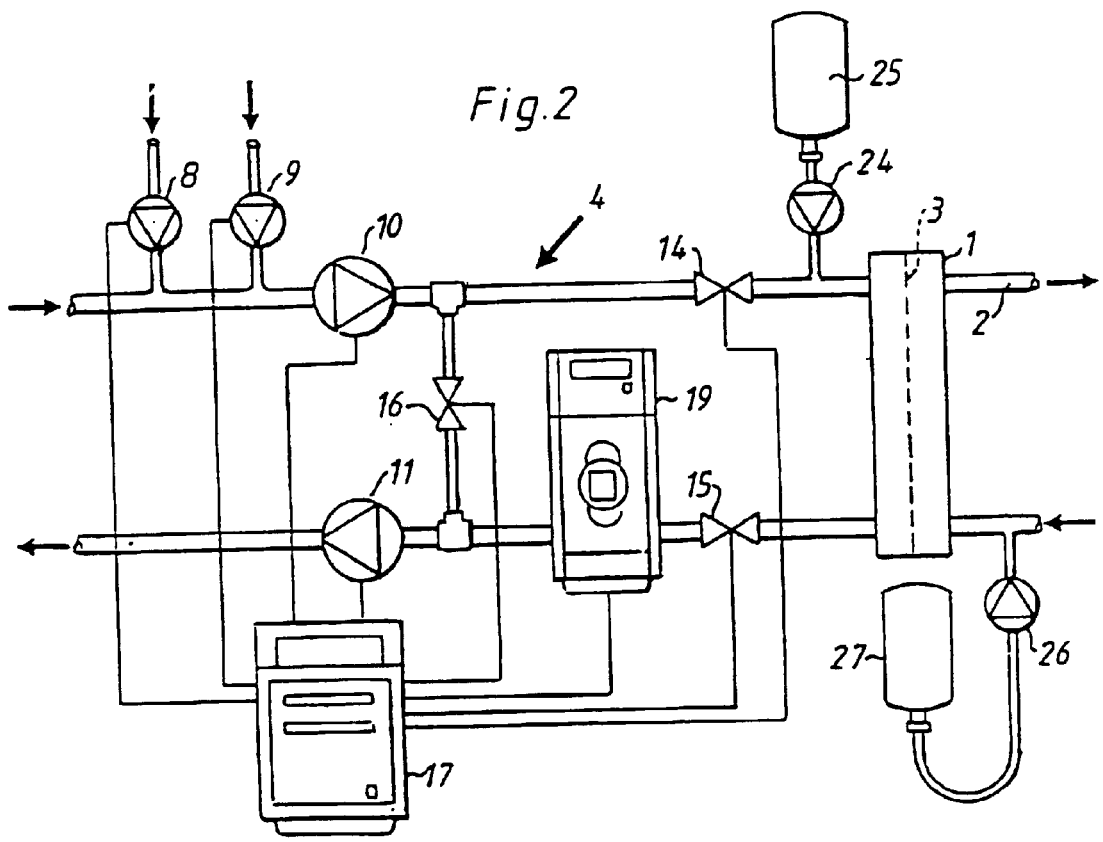
FIG. 2 is a schematic view similar to FIG. 1, but with the urea monitor integrated in the dialysis machine.

FIG. 2 shows a similar dialysis machine as that shown in FIG. 1. The main difference is that the urea monitor 19 is placed between the dialyser 1 and the second main pump 11 and before the outlet of the bypass line.

Figure 3:
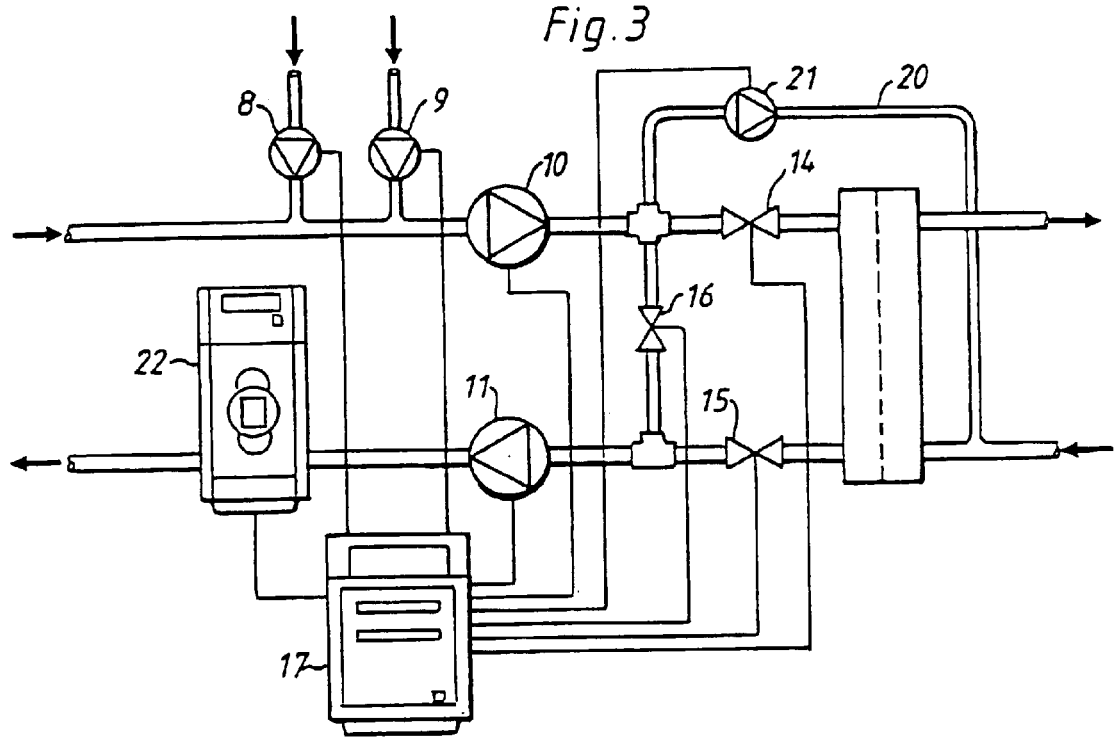
FIG. 3 is a schematic view similar to FIG. 1 of a dialysis machine adapted for predilution hemofiltration.

FIG. 3 discloses a similar dialysis machine as that of FIG. 1, but adapted for hemofiltration or hemodiafiltration. The only difference is that there is included an infusion line 20 including an infusion pump 21. The infusion line 20 starts from the outlet of the first main pump 10 and ends at the blood inlet side of the dialyser, for providing an infusion fluid to the blood before the dialyser, called predilution. The urea monitor 22 is arranged in the effluent dialysate line after the second pump 11.

Figure 4:
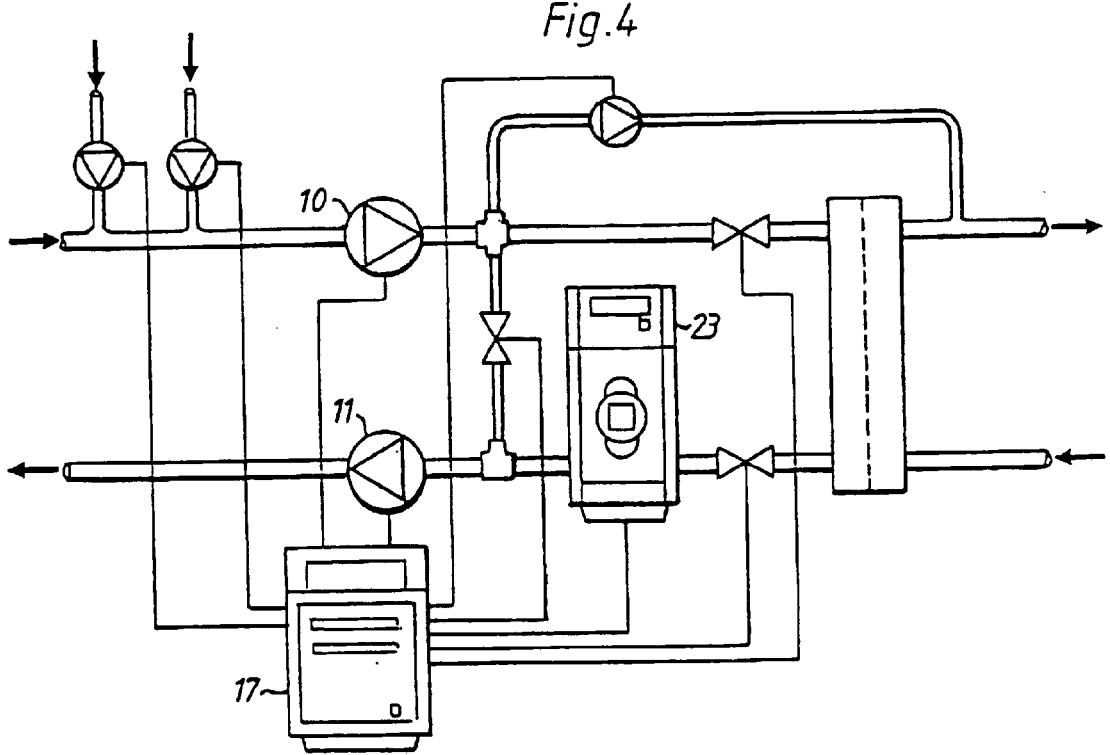
FIG. 4 is a schematic view similar to FIG. 2 of a dialysis machine adapted for postdilution hemofiltration.

FIG. 4 discloses a similar dialysis machine as that of FIG. 2, but adapted for hemofiltration or hemodiafiltration and providing an infusion fluid to the blood after the dialyser, called postdilution. The urea monitor 23 is placed before the second main pump 11 and before the outlet of the bypass line.

Finally, FIG. 5 discloses a typical urea concentration curve $C_d$ obtained from the urea monitor. As appears from the figure, the curve is very irregular and includes several dips. These dips reflect when the dialysis machine is connected for self-calibration, in which valve 16 is opened and valves 14 and 15 are closed.

For operation of the invention according to Swedish Patent Application No. 9702074-7, reference is made to that application, which is incorporated herein by reference thereto. The result is that the urea monitor provides a removed urea concentration curve $c_d$ as disclosed in FIG. 5. The initial values, for example values obtained from about 5 minutes to about 20 minutes, are used for extrapolating an initial urea concentration $c_{d0}$ at the start of the dialysis treatment.

The start of the dialysis treatment is defined as the time when the urea concentration is steadily above a predetermined low concentration value. The actual determination of concentration values is initiated five minutes after determining such a steady condition in order to be sure that the treatment is going on and will not be discontinued.

In order to obtain a measurement of the effective dialyses of the dialyser, a disturbance is induced in the fresh dialysate by operating the pumps, 8 and 9, controlled by the computer 17. The disturbance is generated when the dialysis treatment is in a steady state and may be a change in the ionic content of the dialysis fluid. Such a disturbance may be generated by operating both pumps, 8 and 9, and increasing the speed of these pumps by, for example, 10% during a period of 60 seconds.

The resultant disturbance is measured after the dialyser, for example by a conductivity meter, and the measurement which results is processed, for example, in the manner described in European Application No. 658,352 to obtain the effective dialysance $K_e$. The measurement is performed as soon as possible and preferably after the initial 20 minutes and without changing any of the parameters influencing the dialysance of the dialyser, such as blood flow rate and dialysate flow rate. European Application No. 658,352 is incorporated herein by reference thereto.

If the disturbance is a step change in the conductivity, produced by pumps, 8 and 9, the dialysance of the dialyser can be determined according to the following equation (see European Application No. 547,025, the contents of which is incorporated herein by reference thereto):

$$D_e = Q_d[1-(c_{dout2}-c_{dout1})/(c_{din2}-c_{din1})]$$

where
$D_e$=effective dialysance of the dialyser
$Q_d$=effluent dialysate flow
$c_{dout1}$ and $cut_{dout2}$=concentration in the effluent dialysate
$c_{din1}$ and $c_{din2}$=concentration in the introduced dialysis fluid The concentrations may be sodium concentrations or conductivity of the dialysate.

Indexes 1 and 2 indicate times before and after the step change. The introduced concentration can be measured before the dialyser or can be determined by the set values of the concentration pumps.

The value of the effective dialysance is used for determining the initial urea concentration in the blood at the start of the treatment according to the formula:

$$c_{pw0} = Q_d \times c_{d0}/K_e$$

The plasma urea concentration can then be corrected for protein content in the blood. This correction is fairly constant for the normal range of protein concentrations, which allows the use of the same correction factor for all patients, although the best accuracy is achieved if the true protein content is used.

It is noted that the urea monitor includes a conductivity meter, which may be used for measuring the conductivity after the dialyser, so that there need not be any separate conductivity meter after the dialyser for the measurement according to the present invention.

Instead of measuring the conductivity before the dialyser, the set values of the disturbance can be used.

The disturbance may be induced in different manners.

One approach is to use a small dose of urea, which is introduced in the fresh dialysis fluid just before the entrance into the dialyser as disclosed in FIG. 2. A pump 24 is connected to the inlet of the dialyser downstream of valve 14. The pump is also connected to a small bag 25 containing a predetermined quantity of urea dissolved in water or dialysis fluid (or an isotonic solution) and having a predetermined concentration.

The disturbance induced by this introduction of a known amount of urea in the dialysis circuit is measured by the urea monitor downstream of the dialyser and the result is evaluated by the computer 17. By integrating the measured urea concentration due to the disturbance, the mass of urea reaching the urea monitor can be calculated by multiplication with the flow rate $Q_d$. The difference from the amount introduced, which is known, must have passed through the membrane of the dialyser into the blood of the patient. Thus, the effective dialysance $D_e$ or the effective clearance $K_e$ for urea of the dialyser can be calculated, according to the following formula:

$$D_e = Q_d \times (1 - S_{out}S_{in})$$

where:
$D_e$=effective dialysance of the dialyser
$Q_d$=dialysate flow emitted from the dialyser
$S_{out}$=integral of (cd(t)–cd0) during the disturbance in the flow emitted from the dialyser
$S_{in}$=integral of (cd(t)–cd0) during the disturbance in the flow entered into the dialyser The best accuracy is obtained if the dialysate flow $Q_d$ is constant, i.e. that the flow rate is compensated for the fluid added to the inlet of the dialyser as indicated more in details below.

Of course, the bag 25 may include sodium ions instead of urea and the conductivity mete of the urea monitor may be used for measuring the increased conductivity due to the introduction of extra sodium ions. It is known that the clearance for sodium ions is approximately equal to the clearance of urea. Other types of ions or substances can also be used as well as decreases instead of increases of the concentration or conductivity of the fresh dialysis solution.

If pure water is added, i.e. water without any ions or other substances, the integral given above will be negative, and the surface will have a relationship with the amount of added water.

It is noted that the integral $S_{in}$ times the dialysis fluid flow equals the amount of material added to the solution. Thus, if urea is added, $S_{in}$ need not be measured but can be calculated from the known amount of urea and the dialysis fluid flow. A correction for dilution may also be required.

The same applies if sodium is used, whereby $S_{in} \times Q_{din}$ equals the addition of material in excess of the normal amount, which is normally known in advance.

It is also apparent that the material can be added in any way that enables the measurement at the outlet side of the dialyser, i.e. the disturbance need not be rectangular, but can have any shape. Thus, the introduction flow rate of the material in the dialysate flow is of no importance as soon as it is of such a flow rate that the resultant disturbance is not too small to be measured and not to large to be outside the measuring capability of the measurement instrument at the outlet side of the dialyser. Of course, the disturbance must also be compatible with the body.

The added material can be dissolved in water, whereby the dilution effect should be considered when introducing the material in the circuit. Another approach would be to dissolve the material in normal dialysis fluid, for example to dissolve a known amount of urea in a known amount of dialysis fluid. This dissolution can be performed in advance, so that the material is delivered in bag 25 to be connected to the dialysis circuit. Alternatively, the material can be delivered in powder form, for example a known amount of urea in powder form in a bag 25. The bag is connected to the dialysis machine, and the pump 24 is operated to introduce a known amount of dialysis fluid in the bag to dissolve the amount of material. After dissolution, the pump 24 is reversed and the material in the bag is introduced into the circuit.

The main pump 16 can be operated so that the total amount of fluid entering the dialyser is constant, i.e. the flow rate of pump 16 and pump 24 is constant. For example, if pump 24 is operated at a speed of 50 ml/min, pump 16 is reduced to 450 ml/min during the introduction period and returned to 500 ml/min after introduction of the substance.

Alternatively, the disturbance may be introduced at the other side of the membrane as suggested in FIG. 2 by pump 26 and bag 27. In the same way as with pump 24 and bag 25, introduction of urea of a known concentration and/or amount will result in an increase of the urea concentration in the dialysate reaching the urea monitor. This disturbance can be integrated and processed for obtaining the clearance of the dialyser.

The added material can be fresh dialysis fluid obtained from the dialysis machine, but of a higher (or lower) ionic strength or osmolarity, whereby the conductivity is measured. Alternatively, fresh dialysis fluid can be added, which comprises no urea, and the resulting diluting effect on urea in blood can be determined on the dialysate side by the urea monitor.

The added material, such as urea can be diluted in water or dialysis fluid as indicated above. Moreover, the material can be delivered in powder form in a bag 27 and dissolved in blood by reversing pump 26 and introducing blood in the bag for dissolution of the material and then operating the pump 26 in the normal direction for introducing the material in the circuit.

The time of the measurement may be shortened by using the exponential behaviour of the disturbance for calculating the result as stated in European Application No. 658,352.

When using the integral method, the time may be shortened in the same way by estimating the error when the measurement is terminated in advance.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of calculating the concentration of a first predetermined substance in the blood of a mammal comprising passing said blood through one side of a semipermeable membrane in a dialyser and passing a dialysis fluid on the other side of said semipermeable membrane in said dialyser to provide a dialysate, measuring the concentration of said first predetermined substance in said dialysate, introducing a disturbance in said dialyser by changing the concentration of a second predetermined substance in said dialysis fluid, wherein said first and second predetermined substances are not the same, measuring the change in the concentration of said second predetermined substance in said dialysate, calculating an effective dialysance of said dialyser based on said disturbance, and calculating the concentration of said first predetermined substance in said blood based upon said effective dialysance.

2. The method of claim 1 including determining the flow rate of said dialysate, and wherein said calculating of said concentration of said first predetermined substance in said blood comprises multiplying said measured concentration of said first predetermined substance in said dialysate by said flow rate of said dialysate to provide a product and dividing said product by said effective dialysance.

3. The method of claim 2 wherein said measuring of said concentration of said first predetermined substance in said dialysate is utilized to obtain a curve of said concentration over time, and including calculating an initial mass of said first predetermined substance in a body of said mammal, calculating an initial concentration of said first predetermined substance in said blood, and calculating a distribution volume of said first predetermined substance in said body by dividing said initial mass by said initial concentration of said first predetermined substance in said blood.

4. The method of claim 1 wherein said second predetermined substance comprises a substance selected from the group consisting of sodium ions and a conductivity altering substance.

5. A method of calculating the concentration of a first predetermined substance in the blood of a mammal comprising passing said blood through one side of a semipermeable membrane in a dialyser and passing a dialysis fluid on the other side of said semipermeable membrane in said dialyser to provide a dialysate, determining the flow rate of said dialysate, measuring the concentration of said first predetermined substance in said dialysate, introducing a disturbance in said dialyser comprising adding a predetermined amount of a second predetermined substance into said dialysis fluid, wherein said first and second predetermined substances are different, calculating an effective dialysance of said dialyser based on said disturbance, determining the amount of said second predetermined substance in said dialysate by multiplying a concentration of said second predetermined substance in said dialysate with said flow rate of said dialysate to obtain a product and integrating said product over time, and wherein said calculating of said effective dialysance comprises multiplying said flow rate of said dialysate with a fraction comprising 1 minus said amount of said second predetermined substance in said dialysate over said amount of said second predetermined substance in said dialysis fluid.

6. The method of claim 5 wherein said first predetermined substance comprises urea.

7. Apparatus for calculating the concentration of a first predetermined substance in the blood of a mammal comprising a dialyser including a semipermeable membrane, means for passing said blood over one side of said semipermeable membrane in said dialyser, means for passing a dialysis fluid over the other side of said semipermeable membrane in said dialyser to produce a dialysate, concentration measuring means for measuring the concentration of said first predetermined substance in said dialysate, disturbance means for introducing a disturbance in said dialyser comprising means for changing the concentration of at least a second predetermined substance in said dialysis fluid, a measuring means for measuring the change in the concentration of said second predetermined substance in said dialysate, calculating means for calculating an effective dialysance of said dialyser based on said disturbance, and concentration calculating means for calculating the concentration of said first predetermined substance in said blood based on said effective dialysance, said first and second predetermined substances being different substances.

8. The apparatus of claim 7 including flow rate means for obtaining the flow rate of said dialysate, said concentration calculating means comprising means for multiplying said concentration of said first predetermined substance in said dialysate by said flow rate of said dialysate to provide a product, and dividing said product by said effective dialysance of said dialyser.

9. The apparatus of claim 8 wherein said concentration measuring means comprises means for measuring said concentration of said first predetermined substance in said dialysate to obtain a concentration curve, and including mass calculating means for calculating an initial mass of said first predetermined substance in said mammal, initial concentration calculating means for measuring an initial distribution volume of said first predetermined substance in said mammal, and distribution volume calculating means for measuring the initial distribution volume of said first predetermined substance in said mammal.

10. The apparatus of claim 7 wherein said second predetermined substance comprises a substance selected from the group consisting of sodium ions and a conductivity altering substance.

11. The apparatus of claim 10 wherein said first predetermined substance comprises urea.

12. Apparatus for calculating the concentration of a first predetermined substance in the blood of a mammal comprising a dialyser including a semipermeable membrane, means for passing said blood over one side of said semipermeable membrane in said dialyser, means for passing a dialysis fluid over the other side of said semipermeable membrane in said dialyser to produce a dialysate, concentration measuring means for measuring the concentration of said first predetermined substance in said dialysate, disturbance means for introducing a disturbance in said dialyser comprising means for introducing a predetermined amount of a second predetermined substance into said dialysis fluid flow rate means for measuring the flow rate of said dialysate, calculating means for calculating an effective dialysance of said dialyser based on said disturbance, and concentration calculating means for calculating the concentration of said first predetermined substance in said blood based on said effective dialysance, said first and second predetermined substances being different substances, said concentration measuring means comprising means for measuring the concentration of said second predetermined substance in said dialysate, and including amount determining means for determining the amount of said second predetermined substance in said dialysate by multiplying said concentration of said second predetermined substance in said dialysate with said flow rate of said dialysate to provide a product and integrating said product over time, and wherein said calculating means comprises means for multiplying said flow rate of said dialysate by a fraction comprising 1 minus said amount of said second predetermined substance in said dialysate over the concentration of said second predetermined substance in said dialysis fluid.

* * * * *

UNITED STATES PATENT AND TRADEMARK OFFICE
CERTIFICATE OF CORRECTION

PATENT NO. : 6,861,266 B1
DATED : March 1, 2005
INVENTOR(S) : Jan Sternby

It is certified that error appears in the above-identified patent and that said Letters Patent is hereby corrected as shown below:

Column 2,
Line 6, after "in" insert -- European Application No. 658,352, filed by Hospal AG. --
Line 39, after "of" insert -- European Application No. 658,352 or a similar method, --

Column 8,
Line 2, replace "mete" with -- meter --

Column 10,
Line 51, replace "distribution volume" with -- concentration --
Line 53, replace "the" with -- an --

Signed and Sealed this

Tenth Day of May, 2005

JON W. DUDAS
*Director of the United States Patent and Trademark Office*